(12) United States Patent
Chang et al.

(10) Patent No.: US 8,715,700 B2
(45) Date of Patent: May 6, 2014

(54) ALPHA HYDROXY ACID SUSTAINED RELEASE FORMULATION

(75) Inventors: Yunik Chang, Sonoma, CA (US); Nayan Desai, Santa Rosa, CA (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 968 days.

(21) Appl. No.: 11/490,896

(22) Filed: Jul. 21, 2006

(65) Prior Publication Data

US 2008/0020005 A1    Jan. 24, 2008

(51) Int. Cl.
*A61K 8/02* (2006.01)
*C12P 7/40* (2006.01)

(52) U.S. Cl.
USPC .......................................... 424/401; 435/136

(58) Field of Classification Search
USPC ....................................................... 424/401
See application file for complete search history.

(56) References Cited

U.S. PATENT DOCUMENTS

| | | |
|---|---|---|
| 5,407,958 A | 4/1995 | Heath |
| 5,652,266 A | 7/1997 | Bobier-Rival |
| 5,759,558 A | 6/1998 | Epstein |
| 5,804,203 A | 9/1998 | Hahn |
| 5,817,155 A | 10/1998 | Yasuda |
| 5,863,461 A | 1/1999 | Ansmann |
| 6,162,774 A | 12/2000 | Charlton |
| 6,419,937 B1 | 7/2002 | Waldmann-Laue |
| 6,709,663 B2 * | 3/2004 | Espinoza ...................... 424/401 |
| 7,030,985 B2 | 4/2006 | Jager-Lezer |
| 2004/0247539 A1 | 12/2004 | Wendel |
| 2005/0059644 A1 | 3/2005 | Rood |

OTHER PUBLICATIONS (Croda Naturally Right Chemistry).*
Vaughn, CD, "Using solubility parameters in cosmetics formulation", J. Soc. Cosmet. Chem., 36:319-333 (1985).

* cited by examiner

*Primary Examiner* — Layla Soroush
(74) *Attorney, Agent, or Firm* — Kilpatrick Townsend & Stockton LLP

(57) ABSTRACT

An oil-in-water emulsion containing one or more alpha hydroxy acids in which the oil phase of the emulsion contains a high proportion of polar constituents. The emulsion, even at high concentrations of alpha hydroxy acid, is not irritating when applied to the skin.

38 Claims, No Drawings

ALPHA HYDROXY ACID SUSTAINED RELEASE FORMULATION

FIELD OF THE INVENTION

The present invention pertains to the field of topical formulations for moisturizing skin. In particular, the present invention pertains to the field of topical formulations containing one or more alpha hydroxy acid, a compound useful in the treatment of various disorders including dry skin.

BACKGROUND OF THE INVENTION

Alpha hydroxy acids (AHA) are a class of organic chemical compounds that contain at least one hydroxyl group and at least one carboxyl group, and wherein the hydroxyl group is located on the alpha carbon atom. Included within the AHAs are lactic acid, glycolic acid, citric acid, malic acid, and tartaric acid. Lactic acid and glycolic acid are the AHAs that are most commonly present in topically applied dermatologic formulations. Other AHAs include tartronic acid, glucuronic acid, pyruvic acid, 2-hydroxyisobutyric acid, 3-hydroxybutyric acid, galacturonic acid, mandelic acid, mucic $\alpha$-phenyllactic acid, $\alpha$-phenylpyruvic acid, saccharic acid, $\alpha$-hydroxybutyric acid, $\alpha$-hydroxyisobutyric acid, $\alpha$-hydroxyisocaproic acid, $\alpha$-hydroxyisovaleric acid, atrolactic acid, galactanic acid, pantoic acid, glyceric acid, isocitric acid, dihydroxymaleic acid, dihydroxytartaric acid, dihydroxy-fumaric acid and benzylformic acid.

Formulations containing an alpha hydroxy acid (AHA) have long been used by dermatologists and other skin-care professionals in the treatment of certain skin disorders, such as dry skin, including xerosis and ichthyoses. AHAs have been shown to have beneficial moisturizing, keratolytic, and exfoliant effects. There is also evidence that AHAs stimulate collagen and elastin production and are reported to improve wrinkling, roughness, and mottled pigmentation of skin.

One problem with presently available formulations of AHA is that they often cause irritation to skin. The irritation due to the AHA is primarily due to the presence of the AHA itself and of the low pH of these formulations. For example, glycolic acid has a pKa of 3.8. Therefore, in a formulation at this pH, 50% of the glycolic acid will be ionized and 50% will be non-ionized. At pH lower than the pKa, higher proportions of the AHA will be in the non-ionized form and at pH higher than the pKa, higher proportions of the AHA will be in the ionized form.

Because the AHAs perform their desirable dermatologic functions better in the non-ionized form, the products are formulated at as low a pH as is practical. The low pH is irritating to skin. Additionally, high concentrations of AHA are directly irritating to skin. In fact, when used in concentrations of 20% or higher that are effective as a chemical peel to remove scars and wrinkles, redness and stinging associated with this type of therapy can endure for several weeks following treatment.

Epstein, U.S. Pat. No. 5,759,558 discloses an emulsion containing an AHA, a quaternary ammonium cationic emulsifier, and petrolatum or mineral oil. The emulsion of Epstein may also contain one or more of a fatty alcohol having a carbon chain length between $C_{12}$ to $C_{32}$, in a concentration of 1 to about 8 weight %, a fatty ester emollient at this same concentration range, and a silicone oil at a concentration of 0.1 to 5 weight %.

Hahn, U.S. Pat. No. 5,804,203, discloses compositions containing an AHA. In order to reduce the skin irritation associated with the AHA, the compositions include an aqueous soluble cation of strontium ($Sr^{2+}$) in a concentration effective to prevent or reduce the skin irritation due to the AHA. The concentration of strontium ion in the composition needed to achieve this anti-irritant effect is 50 mM or more, although this concentration of strontium can be halved if appropriate levels of a calcium channel blocking agent, a sodium channel blocking agent, or a steroidal or non-steroidal anti-inflammatory compound is included in the composition.

Bobier-Rival, U.S. Pat. No. 5,652,266, discloses a composition containing three active ingredients; an AHA, salicylic acid, and a retinoid. As disclosed in Bobier-Rival, the use of these three ingredients in combination permits lower concentrations of an AHA to be used and so reduces the irritating effects of the AHA.

Charlton, U.S. Pat. No. 6,162,774, discloses that the combination of an AHA in a detergent base comprising a mixture of a non-ionic alkylpolyglucoside surfactant and an amphoteric surfactant reduces irritation and enables compositions to be formulated at low pH between 3.0 and 4.5. The invention of Charlton is disclosed to be effective, however, with concentrations of AHA only up to 10%.

Heath, U.S. Pat. No. 5,407,958, discloses a therapeutic composition that contains one or more AHAs and a preservative, sodium hydroxymethylglycinate, which is provided in the composition to neutralize the AHA and reduce skin irritation. The compositions of Heath also contain a silicone, such as cyclomethicone and/or dimethicone, and may contain branched chain hydrocarbons. The pH of the Heath compositions is higher than 5.0.

Merz Pharmaceuticals, LLC (Greensboro, N.C.), markets a line of skin care products containing glycolic acid (Aqua Glycolic®). These products include a facial cleanser containing 12% glycolic acid, a toner containing 11% glycolic acid, a face cream containing 10% glycolic acid, a shampoo & body cleanser containing 14% glycolic acid, and a hand & body lotion containing 14% glycolic acid. Irritation is a problem with these products. With each of these products, a user is instructed to watch for irritation and to use these products only once daily, and to only increase to twice daily if there is no irritation.

Upsher-Smith Laboratories, Inc. (Minneapolis, Minn.) markets a line of skin care products containing 12% lactic acid (AmLactin®). These products are the commercial embodiment of the invention disclosed in Rood, U.S. Patent Publication 2005/0059644. The AmLactin® products contain, in addition to the AHA in its acid form, an ammonium salt of the AHA which raises the pH of these products to between 4.5 and 5.5. Possibly due to the high pH of these products, they have been shown to have very low irritancy potential. One disadvantage of these products and their high pH is that AHAs perform better when the AHA is in a non-ionized form, and the percentage of the non-ionized form relative to the ionized form of the AHA decreases with increasing pH. Therefore, it would be advantageous to provide a non-irritating formulation of an AHA that is at a pH of 4.0 or lower.

A significant need remains for a non-irritating formulation of an AHA, especially one that has a concentration of higher than 10% and which can be used safely multiple times daily.

DESCRIPTION OF THE INVENTION

It has been discovered that, by providing an alpha hydroxy acid (AHA) in a topical formulation from which the AHA is released slowly to the skin upon application, irritation to the skin due to the presence of the AHA can be greatly reduced.

Such a formulation may be prepared as an oil-in-water emulsion in which a substantial proportion of the AHA is partitioned in the oil phase.

Because AHAs are very polar molecules, they are highly soluble in water and only sparingly soluble in oil. However, the solubility or oil-water partition of an AHA in an oil-in-water emulsion may be influenced by the polarity of the vehicles of the emulsion. For example, glycolic acid is very soluble in ethyl acetate ester and is only slightly soluble in ethyl ether. The higher solubility of glycolic acid in the ester is due to the relatively higher polarity of the ester compared to the ether. This is true even though the carbon chain length of the ether is very short. The present invention is based upon the increased partitioning of an AHA in the oil phase of an emulsion due to increasing the polar nature of the oil phase.

It has been unexpectedly discovered that, by increasing the proportion of an AHA in an oil-in-water emulsion that is dissolved in the oil phase of the emulsion, skin irritation due to application of the emulsion to the skin is markedly reduced. The proportion of the AHA that is dissolved in the oil phase of a oil-in-water emulsion may be increased by utilizing one or more polar oil solvents in the oil phase and by limiting the concentration of non-polar constituents in the oil phase.

Although not wishing to be bound by theory, the inventors conceive that an emulsion in which a high proportion of the AHA is dissolved in the oil phase provides two sources of the AHA that are released from the emulsion at different rates. The AHA that is dissolved in the water phase of the emulsion is delivered to the skin upon application. The AHA that is dissolved in the oil phase of the emulsion, however, is released at a slower rate from the emulsion. This slower release of the AHA from the emulsion provides a diminution in irritation potential of the AHA without decreasing the effectiveness of the AHA in treating the skin.

In one embodiment, the invention is an oil-in-water emulsion containing an alpha hydroxy acid, wherein the oil phase of the emulsion contains a high proportion of polar constituents relative to non-polar constituents. Generally, the oil phase of the emulsion is between 5% and 40% w/w of the total emulsion. In accordance with this embodiment of the invention, at least 80% w/w of the constituents of the oil phase is polar. Preferably, at least 85% of the constituents of the oil phase are polar. More preferably, at least 90% of the constituents of the oil phase are polar. It is most preferred that at least 95% of the constituents of the oil phase are polar and, in a particularly most preferred embodiment, 100% of the constituents of the oil phase are polar. Preferably, the concentration of alpha hydroxy acid as a percentage of the emulsion is 8.0% w/w or greater, more preferably 10.0% or greater, and most preferably 12.0% or greater.

As used herein, the percentages of the oil phase and water phase of the emulsion relative to the total phase of the emulsion or the percentages of the constituents of the oil phase are calculated based on the amounts of ingredients that are used to formulate the emulsion, and not by determining the concentration of the ingredients of the emulsion or the individual phases of the emulsion after the emulsion or after the individual phases have been formulated. An ingredient of the emulsion is considered to be part of the water phase of the emulsion if it has a partition coefficient between water and octanol higher than 9.0 at room temperature. Conversely, an ingredient is considered to be a part of the oil phase of the emulsion if the partition coefficient is less than 0.1. For purposes of the present invention, ingredients that are distributed between both the oil and water phases of an emulsion, those having a partition coefficient between 9.0 and 0.1, are not considered when determining the constituents of the oil phase.

As used herein, the term "polar" as it relates to constituents of the oil phase of an oil-in-water emulsion refers to a chemical compound that has a solubility parameter of 7.5 or higher as calculated by the method of Hildebrand, as disclosed in Vaughan, C D, Journal Society Cosmetic Chemists, 36:319-333 (September/October 1985). A "non-polar" chemical compound, as used herein, is one that has a solubility parameter less than 7.5.

Any alpha hydroxy acid (AHA), or combination of AHAs, is suitable for the emulsion of the invention. Preferred AHAs include lactic acid, glycolic acid, citric acid, malic acid, and tartaric acid. Most preferred AHAs are lactic acid and glycolic acid. The invention is described in further detail below primarily with reference to glycolic acid. It will be understood by those skilled in the art that the invention is applicable also to other AHAs, including the preferred AHAs such as lactic acid.

If desired, the emulsion of the invention may include strontium, which is disclosed in U.S. Pat. No. 5,804,203 as reducing irritation caused by formulations containing an AHA. However, it has been discovered that the emulsions of the present invention are non-irritating even without the inclusion of strontium in the emulsion. Therefore, although strontium may be present in the emulsion, it is an optional ingredient. It is preferred that the emulsion of the invention is substantially free of strontium. As used herein, "substantially free of strontium" means that the concentration of strontium in the emulsion is below that which if effective to reduce skin irritation due to the presence of one or more AHAs in the emulsion. As disclosed in the U.S. Pat. No. 5,804,203, the effective concentration of strontium is 50 mM or higher unless an additional anti-irritant component is included in the formulation, in which case the effective concentration of strontium is 25 mM or higher. It is more preferred that the emulsion of the invention does not have a concentration of strontium of 10 mM or higher, and is most preferred to be free of strontium.

The aqueous phase of the emulsion may optionally contain constituents in addition to one or more AHAs. Such constituents, which are immaterial to the present invention, may include ingredients found in topical pharmaceutical formulations, such as preservatives, gelling agents, stabilizers, preservatives, buffers, foaming agents, skin penetration enhancers such as propylene glycol, and humectants such as glycerin or urea.

It is preferred that the oil phase of the emulsion is free of non-polar oils such as mineral oil, petrolatum, and silicone oils because these non-polar oils hinder the polar interaction of AHAs, resulting in reducing partitioning of an AHA into the oil phase. However, if one or more non-polar oils are present in the emulsion, it is preferred that the relative concentration w/w of polar oil to non-polar oil in the emulsion is at least 4:1, and preferably at least 10:1.

As used herein, the term "polar emollient" is synonymous with "polar oil" and is a lipid soluble chemical compound that has a solubility parameter of 7.5 or higher. Polar emollients that are suitable for the emulsion of the invention include fatty alcohols, preferably short or medium chain fatty alcohols having a carbon length of up to 18, medium or short chain fatty acid triglycerides, esters such as fatty acid esters, and lecithins and related polar compounds such as phosphatidylcholine, phosphatidylethanolamine, phosphatidylserine, phosphatidylinositol, phosphatidic acid, lyso-phosphatidylcholine, lyso-phosphatidylethanolamine, and sphingomyelin.

Particular examples of polar oils that are suitable for the emulsion of the invention include triglyceride oils like vegetable oils such as wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, quinoa, olive, rye, safflower, candlenut, soya, palm, passion flower, or musk rose oil; triglycerides of caprylic/capric acid, such as those sold under the tradenames MIGLYOL® (Condea Chemie, Germany) and CRODAMOL (Croda, Inc., Edison, N.J.); fatty alcohols such as caprylic alcohol, lauryl alcohol, myristyl alcohol, cetyl alcohol, and stearyl alcohol; and fatty esters such as oleyl acetate, isotridecyl benzoate, diisooctyl sebacate, isopropyl myristate, cetyl octanoate, isopropyl palmitate, butyl stearate, hexyl laurate, myristyl myristate, decyl oleate, hexyldecyl dimethyloctanoate, cetyl lactate, myristyl lactate, lanoline acetate, isocetyl stearate, isocetyl isostearate, cholesteryl 12-hydroxystearate, dipentaerythritol fatty acid ester, and isostearyl malate.

The oil phase also contains an emulsifier at a concentration relative to the total of the emulsion of up to 20% w/w, preferably 10% w/w or less. In a preferred embodiment, the emulsifier is a cationic emulsifier. In a less preferred embodiment, the emulsifier is a non-ionic emulsifier or a combination of a non-ionic and a cationic emulsifier. Preferably, the emulsion is free of strong anionic emulsifiers. However, weak anionic emulsifiers, such as Crodafos® CES (Croda, Inc., New York) are suitable. As defined herein, a "weak anionic emulsifier" is one that is 0.1% or less ionized at a pH of 4.0 based on Henderson-Hasselbach calculation. Conversely, as defined herein, a "strong anionic emulsifier" is one that is greater than 0.1% ionized at a pH of 4.0. Crodafos® CES is a weak anionic emulsifier containing a combination of cetearyl alcohol, ceteth-10 phosphate, and dicetyl phosphate. At a pH of 4.0, Crodafos® CES is about 0.08% ionized and, therefore, is basically neutral with a very minor anionic property.

Suitable cationic emulsifiers include fatty amines; quaternary ammonium compounds; as well as cationic copolymers, cationic mixed polymers, cationic polysaccharides, cationic cellulose derivatives, cationic or cationized hydrolyzed proteins such as collagen or keratin, or a mixture thereof. Specific examples of cationic emulsifiers include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof; quaternary esters, such as tetradecylbetaine ester chloride; diquaternary esters, such as dipalmitoylethyldimethylammonium chloride; and diquaternary silicones.

Non-ionic emulsifiers include cetearyl alcohol, ceteth-10, cetyl alcohol, and butylene glycol. A preferred non-ionic emulsifier is emulsifying wax, mixtures of fatty acids of about 12 to 24 carbon atoms in length. Emulsifying waxes that are preferred are those that meet the standards of the National Formulary (N.F.). A preferred N.F. grade emulsifying wax is prepared from cetostearyl alcohol containing a polyoxyethylene derivative of a fatty ester of sorbitan. Emulsifying Wax N.F. is available from several manufactures, for example the emulsifying waxes sold under the trade names POLAWAX™ (Croda, Inc., NY) and LIPOWAX™ (Lipo Chemicals, Inc., Paterson, N.J.).

Preferably, but not necessarily, the pH of the composition of the invention is within 1.0 pH units of the dissociation constant (pKa) of the AHA in the composition, or of the combined pKa of the AHAs if more than one AHA is present. If desired, the pH may be higher or lower than 1.0 pH units of the pKa of the AHA. More preferably, the pH is within 0.5 pH units of the pKa. Because it is known that the therapeutic effect of an AHA is maximized when the AHA is non-ionized, it would therefore appear to be optimal for the composition to have a pH below the pKa of the AHA in the composition. However, as pH is decreased too low, the formulation becomes irritating to skin due to the acidity of the formulation. Therefore, determining the preferred pH of the composition is necessarily a compromise between the desire for a low pH to optimize the function of the AHA and for a higher pH to reduce skin irritation due to acidity. Accordingly, a preferred pH for the composition containing glycolic acid, which has a pKa of 3.8, is between 2.8 and 4.8 and a most preferred pH is between 3.3 and 4.3.

The emulsion of the invention may be used to formulate a composition for topical application to the skin. The composition may be in the form of a lotion or a cream. The composition may be in the form of a lipopsome composition suitable for topical administration. The composition may contain an oil-soluble or water-soluble pharmaceutical compound for treatment of a disorder of the skin. The composition containing the emulsion of the invention is applied topically to the skin and is preferably rubbed into the skin to assist in penetration.

It has been discovered that the emulsion of the invention containing AHA is not irritating to skin, even at levels of AHA of 10% w/w or higher. Therefore, if desired, the emulsion of the invention may be applied to skin more than once daily, or two, three, four or more times daily, without irritation.

The invention is further illustrated in the following non-limiting examples.

EXAMPLE 1

Cream

A cream formulation of the invention containing 12% glycolic acid was made containing the ingredients shown in Table 1. The solubility parameters of the constituents of the oil phase, other than emulsifiers, are shown in Table 1.

TABLE 1

| Ingredient Name | Percent w/w | Solubility Parameter |
|---|---|---|
| Glycolic Acid 70% (High Purity) | 12.00 | |
| Behentrimonium Methosulfate and Cetearyl Alcohol (Incroquat Behenyl TMS, Croda, Inc.) | 4.00 | |
| Caprylic/Capric Triglyceride (Crodamol GTCC-PN, Croda, Inc.) | 4.00 | 8.57-8.75 |
| Cetyl Alcohol | 1.00 | 8.93 |
| Emulsifying Wax N.F. | 8.00 | 8.9 |
| Propylene Glycol | 1.00 | |
| Purified Water (part I) | 45.00 | |
| Polyaminopropyl biguanide (Cosmocil ® CQ, Arch Personal Care Products, South Plainfield, NJ) | 0.15 | |
| Sodium Hydroxide | 1.00 | |
| 20% NaOH Solution | q.s. pH to 4.0 | |
| Purified Water (part II) | q.s.ad 100 | |

The purified water (part I), was combined with the propylene glycol, glycolic acid, and sodium hydroxide and the combination was mixed and heated until the mixture reached a temperature of 85°±3° C. and a clear aqueous solution was obtained. In a separate vessel, the behentrimonium methosulfate and cetearyl alcohol, caprylic/capric triglyceride, cetyl alcohol, and emulsifying wax were combined and melted at 85°±3° C. and mixed until a clear oil solution was obtained. The oil solution was added to the aqueous solution and was mixed while cooling the mixture at 25° C. When the temperature reached at or below 40° C., the polyaminopropyl biguanide was added to the mixture, which was mixed further until homogenized. At this time, a sample was obtained and the pH was measured. A quantity of a 20% NaOH solution was added to adjust the pH, if necessary, to 4.0±0.2 and the mixture was mixed again until homogenous. The amount of water (part II) needed to bring the composition to 100% was added and the mixture was further mixed until a cream was obtained that was smooth and homogenous.

EXAMPLE 2

Lotion

A lotion formulation of the invention containing 12% glycolic acid was made containing the ingredients shown in Table 2. The solubility parameters of the constituents of the oil phase, other than emulsifiers, are shown in Table 2.

TABLE 2

| Ingredient Name | Percent w/w | Solubility Parameter |
|---|---|---|
| Glycolic Acid 70% (High Purity) | 12.00 | |
| Dicetyl Phosphate, Cetearyl Alcohol, Ceteth-10 Phosphate (Crodafos CES, Croda, Inc.) | 4.00 | |
| Caprylic/Capric Triglyceride (Crodamol GTCC-PN) | 5.00 | 8.57-8.75 |
| Cetyl Alcohol | 1.00 | 8.93 |
| Steareth-2 | 0.1 | 8.57 |
| Steareth-21 | 0.5 | 9.06 |
| Propylene Glycol | 1.00 | |
| Purified Water (part I) | 60.0 | |
| Cosmocil ® CQ | 0.15 | |
| Sodium Hydroxide | 0.9 | |
| 20% NaOH Solution | qs pH to 4.0 | |
| Purified Water (part II) | q.s.a.d. 100 | |

The purified water (part I), was combined with the propylene glycol, glycolic acid, and sodium hydroxide and the combination was mixed and heated until the mixture reached a temperature of 85°±3° C. and a clear aqueous solution was obtained. In a separate vessel, the dicetyl Phosphate, cetearyl alcohol, and ceteth-10 phosphate, caprylic/capric triglyceride, cetyl alcohol, steareth-2, and steareth-21 were combined and melted at 85°±3° C. and mixed until a clear oil solution was obtained. The oil solution was added with mixing to the aqueous solution and was further mixed for 10 minutes at 85°±3° C. With continuous mixing, the mixture was cooled to 25° C. When the temperature reached at or below 40° C., the polyaminopropyl biguanide was added to the mixture, which was mixed further until homogenized. At this time, a sample was obtained and the pH was measured. A quantity of a 20% NaOH solution was added to adjust the pH, if necessary, to 4.0±0.2 and the mixture was mixed again until homogenous. The amount of water (part II) needed to bring the composition to 100% was added and the mixture was further mixed until a lotion was obtained that was smooth and homogenous.

EXAMPLE 3

Clinical Study

A clinical study was conducted on 10 adult female subjects of various ethnicities to compare subjective facial skin discomfort, such as stinging, burning, itching, and tingling, that occurs due to application of various cream and lotion embodiments of the invention and a prior art composition known to be non-irritating.

Six formulations of the invention, as described in Examples 1 and 2, were tested, each having a pH of about 4.0.

Composition A. 12% AHA cream (Example 1) with 2% strontium. Strontium has been reported to reduce skin irritation due to topical application of an AHA, Composition B. 12% AHA lotion (Example 2) with 2% strontium, Composition C. 12% AHA cream (Example 1) with 1% strontium, Composition D. 12% AHA lotion (Example 2) with 1% strontium, Composition E. 12% AHA cream (Example 1) without strontium, and Composition F. 12% AHA lotion (Example 2) without strontium.

These six formulations were tested in comparison with AmLactin® Cream (Upsher-Smith Labs, Inc., Maple Grove, Minn.), designated Composition G. This product contains 12% lactic acid that is neutralized with ammonium hydroxide to form ammonium lactate. The pH of the AmLactin® Cream is stated on product literature to be between 4.5 and 5.5. A 10% lactic acid solution was utilized as a positive control for skin irritation, and deionized water, designated was used as a negative control for skin irritation.

Prior to each evaluation, the subjects rested in a room with controlled temperature and humidity for about 20 minutes and then placed their faces in a steam sauna for about 2 minutes. For each evaluation, a clinical staff member pipetted 500 microliters of the test material and applied it to the subject's face by briskly rubbing it on the surfaces of the nasolabial folds, along the hairline on the forehead, and on the chin. The subjects assessed the nature and severity of subjective discomfort at 1 minute, 2.5 minutes, 5 minutes, and 8 minutes following application. The discomfort was rated on a discomfort scale, as follows:

0.0—no discomfort or a pleasant sensation
0.5—slight discomfort, barely detectable
1.0—mild discomfort, detectable sensation but tolerable
1.5—mild to moderate discomfort
2.0—moderate discomfort, unpleasant feeling but tolerable
2.5—moderate to severe discomfort
3.0—severe discomfort, intense unpleasant feeling The ten subjects that participated in the study were screened from a larger group of potential subjects to ensure that each of the subjects was sensitive to AHA and was not overly sensitive, that is did not experience discomfort following application of deionized water. Therefore, only subjects that experienced a discomfort of 1.5 or greater to the positive control lactic acid solution and at one or more of the time points and a discomfort of 0.5 or less to the negative control deionized water at all time points were included in the study.

The test materials were applied successively, starting two to ten days following completion of the screening phase, and the evaluation of each successive test material was separated from a previous evaluation by a time of at least 48 hours. Table 3 shows the frequency of reported discomfort scores for each of the test materials and the controls at the assessment times. The number of subjects reporting the indicated level of discomfort is listed.

TABLE 3

| TREATMENT | SCORE | 1 min | 2.5 min | 5 min | 8 min |
|---|---|---|---|---|---|
| Comp. A | 0.0 | 9 | 9 | 10 | 10 |
| 12% AHA cream with 2% strontium | 0.5 | 1 | 1 | 0 | 0 |
| Comp. B | 0.0 | 8 | 6 | 5 | 5 |
| 12% AHA lotion with 2% strontium | 0.5 | 2 | 3 | 4 | 3 |
|  | 1.0 | 0 | 1 | 1 | 2 |
| Comp. C | 0.0 | 6 | 6 | 4 | 6 |
| 12% AHA cream with 1% strontium | 0.5 | 4 | 3 | 5 | 3 |
|  | 1.0 | 0 | 1 | 1 | 1 |
| Comp. D | 0.0 | 7 | 6 | 7 | 7 |
| 12% AHA lotion with 1% strontium | 0.5 | 1 | 2 | 2 | 1 |
|  | 1.0 | 2 | 1 | 0 | 2 |
|  | 1.5 | 0 | 1 | 1 | 0 |
| Comp. E | 0.0 | 9 | 7 | 7 | 8 |
| 12% AHA cream without strontium | 1.0 | 1 | 3 | 3 | 2 |
| Comp. F | 0.0 | 7 | 6 | 6 | 6 |
| 12% AHA lotion without strontium | 0.5 | 3 | 4 | 3 | 3 |
|  | 1.0 | 0 | 0 | 1 | 1 |
| Comp. G | 0.0 | 10 | 10 | 10 | 9 |
| AmLactin® 12% AHA cream | 0.5 | 0 | 0 | 0 | 1 |
| Positive Control | 0.0 | 1 | 0 | 0 | 0 |
| 10% AHA solution | 0.5 | 0 | 1 | 0 | 1 |
|  | 1.0 | 3 | 1 | 0 | 1 |
|  | 1.5 | 2 | 2 | 3 | 1 |
|  | 2.0 | 3 | 4 | 6 | 6 |
|  | 2.5 | 1 | 1 | 0 | 0 |
|  | 3.0 | 0 | 1 | — | — |
| Negative Control | 0.0 | 6 | 6 | 8 | 8 |
| Deionized Water | 0.5 | 4 | 4 | 2 | 2 |

Following the test and scoring above, the highest discomfort scores for every subject, regardless of the time point of occurrence, were averaged. The results are shown in Table 4 which presents the mean scores calculated for the test materials and controls, and statistical comparisons that indicate any significant differences ($p \leq 0.05$) that exist among the test materials and controls. Items in Table 4 are listed in order from least to greatest discomfort. Items indicated by the same symbol in the columns on the right of Table 4 are not significantly different from one another.

TABLE 4

| TREATMENT | MEAN SCORE | NO SIGNIFICANT DIFFERENCE | | |
|---|---|---|---|---|
| Comp. G AmLactin® 12% AHA cream | 0.05 | X X |  |  |
| Comp. A 12% AHA cream with 2% strontium | 0.10 | X X | X X |  |
| Comp. E 12% AHA cream without strontium | 0.20 | X X | X X | X X |
| Comp. F 12% AHA lotion without strontium | 0.30 | X X | X X | X X |
| Negative Control Deionized Water | 0.35 |  | X X | X X |
| Comp. C 12% AHA cream with 1% strontium | 0.40 |  |  | X X |
| Comp. D 12% AHA lotion with 1% strontium | 0.45 |  |  | X X |
| Comp. B 12% AHA lotion with 2% strontium | 0.45 |  |  | X X |
| Positive Control 10% AHA solution | 2.10 |  |  | X X |

As shown in Table 4, all seven test materials, Compositions A to G, produced mean maximum discomfort scores less than 0.5 (slight discomfort, barely detectable). Statistical comparison of mean discomfort scores showed that all test materials, except AmLactin®, produced a mean discomfort score that was significantly lower than water. The results show that the addition of strontium does not produce a significant decrease in discomfort. The results also show that the composition of the invention, especially without strontium, produced discomfort scores that were not statistically different from that of AmLactin®. This result is especially noteworthy when it is considered that AmLactin® is neutralized so that it has a higher pH than do the compositions of the invention, and that a portion of the irritation due to the application of topical products containing AHAs is due to the low pH. The lack of irritation of the compositions of the invention was obtained while maintaining the pH at a level at which AHAs are more effective.

EXAMPLE 4

Repeat Exposure Clinical Study

A clinical study was conducted on 100 adult male and female subjects of various ethnicities to compare irritation following repeated topical application of the cream and lotion of the invention formulated at different pH levels compared with a prior art composition known to be non-irritating and a positive irritation control. The study was conducted in two cohorts of 50 subjects each.

Cohort 1 was conducted on 50 of the subjects, 43 of whom completed the study. This cohort compared irritation due to topical application of a cream of Example 1, a lotion of Example 2, each of which were formulated at a pH of 3.2, AmLactin® Cream (Upsher-Smith Labs, Inc.) (12% lactic acid, neutralized to pH 4.5 to 5.5), and 0.3% sodium lauryl sulfate (SLS) cream (positive mild irritant control). The compositions were applied as occlusive patches for the first 4 to 7 days of the study, depending on subject start date, and then were later applied as semi-occlusive patches.

Cohort 2 was conducted on 50 of the subjects, 47 of whom completed the study. This cohort compared irritation due to topical application of a cream of Example 1 pH 3.2, a cream of Example 1 pH 3.8, a cream of Example 1 pH 4.5, a lotion of Example 2 pH 3.2, a lotion of Example 2 pH 3.8, a lotion of Example 2 pH 4.5, AmLactin® Cream (Upsher-Smith Labs, Inc.), and 0.3% sodium lauryl sulfate (SLS) cream (positive control). The compositions for Cohort 2 were applied as semi-occlusive patches.

Each of the test compositions were applied under separate patches on the back of each subject three times a week for a three week induction period. The patches remained in place for 48 hours (or 72 hours if applied on a Friday), at which time they were observed for signs of irritation or inflammation. Evaluations of irritation were made at least 5 and no more than 15 minutes following removal of the patches. Skin reactions were evaluated using the following scale.

0.0—no sign of irritation
0.5—barely perceptible erythema
1.0—slight erythema
2.0—noticeable erythema with slight infiltration
3.0—erythema with marked edema
4.0—erythema with edema and blistering Cumulative irritation was evaluated by the total of the assessments of the application sites during the induction phase of the study. A total irritation score for each composition was calculated by summing the score for each subject from all evaluation days during the induction phase. The total irritation score for each composition in each cohort had a maximum possible total of 1800 (50 subjects×9 evaluations×4 (maximum daily irritation score)). The test articles were classified according to the total irritation score as shown in Table 5.

TABLE 5

| IRRITANCY CLASSIFICATION | TOTAL IRRITATION SCORE |
|---|---|
| No significant irritation | 0-225 |
| Slightly irritating | 226-675 |
| Moderately irritating | 676-1350 |
| Highly irritating | 1351-1800 |

The results of the irritation study are shown in Table 6.

TABLE 6

| TEST ARTICLE | CUMULATIVE IRRITATION SCORE | CLASSIFICATION |
|---|---|---|
| COHORT 1 | | |
| 0.3% SLS | 262 | slightly irritating |
| Cream of Example 1, pH 3.2 | 1206 | moderately irritating |
| Lotion of Example 2, pH 3.2 | 1226.5 | moderately irritating |
| Amlactin ® Cream (pH 4.5-5.5) | 57 | no significant irritation |
| COHORT 2 | | |
| 0.3% SLS | 52.5 | no significant irritation |
| Cream of Example 1, pH 3.2 | 776 | moderately irritating |
| Cream of Example 1, pH 3.8 | 77 | no significant irritation |
| Cream of Example 1, pH 4.5 | 40.5 | no significant irritation |
| Lotion of Example 2, pH 3.2 | 551 | slightly irritating |
| Lotion of Example 2, pH 3.8 | 49 | no significant irritation |
| Lotion of Example 2, pH 4.5 | 27 | no significant irritation |
| Amlactin ® Cream (pH 4.5-5.5) | 72 | no significant irritation |

The study shows that, at a pH of 3.2, the composition of the invention is slightly irritating and is more irritating than a positive mild irritation control and a prior art composition having a pH of 4.5 to 5.5 and known not to be irritating. The study further shows, however, that at a pH of 3.8, the cream and lotion of the invention were comparable in irritation to the non-irritating prior art composition even though the pH of the compositions of the present invention were significantly lower than that of the prior art composition. At a pH of 3.8, the cumulative irritation scores for both the lotion and the cream of the invention were comparable to or lower than that of the prior art non-irritating composition.

The data establishes that irritation following application of the cream and lotion compositions of the invention is due to the low pH when formulated at a pH less than 3.8 and is not due to the presence of the AHA in the compositions. The data further establishes that, at pH of 3.8 and higher, the composition of the invention is not irritating and produces the same degree of irritation or less than does a prior art composition formulated at pH 4.5 to 5.5 that is known in the art to be non-irritating.

Further modifications, uses, and applications of the invention described herein will be apparent to those skilled in the art. It is intended that such modifications be encompassed in the following claims.

The invention claimed is:

1. An oil-in-water emulsion comprising a contiguous external aqueous phase and droplets consisting of an internal oil phase suspended in the contiguous external phase, which emulsion comprises an alpha-hydroxy acid at a concentration of at least 8.0% w/w, wherein the oil phase of the emulsion comprises a polar emollient and an emulsifier, wherein at least 80% w/w of the constituents of the oil phase of the emulsion, based on the relative amounts of each constituent as used to formulate the emulsion, are polar.

2. The emulsion of claim 1 wherein at least 85% w/w of the constituents of the oil phase of the emulsion are polar.

3. The emulsion of claim 1 wherein at least 90% w/w of the constituents of the oil phase of the emulsion are polar.

4. The emulsion of claim 1 wherein at least 95% w/w of the constituents of the oil phase of the emulsion are polar.

5. The emulsion of claim 1 wherein the oil phase of the emulsion is free of constituents that are not polar.

6. The emulsion of claim 1 wherein the emulsifier is selected from the group consisting of cationic emulsifier, non-ionic emulsifier, and weak anionic emulsifier.

7. The emulsion of claim 1 which is free of strong anionic emulsifiers.

8. The emulsion of claim 1 wherein the concentration of the alpha-hydroxy acid is at least 10% w/w.

9. The emulsion of claim 1 wherein the concentration of the alpha-hydroxy acid is at least 12% w/w.

10. The emulsion of claim 1 which is free of mineral oil, petrolatum, and silicone oil.

11. The emulsion of claim 1 which has a relative concentration by weight of polar emollients to non-polar emollients of at least 4:1.

12. The emulsion of claim 1 which has a relative concentration by weight of polar emollients to non-polar emollients of at least 10:1.

13. The emulsion of claim 1 which is free of non-polar emollients.

14. The emulsion of claim 1 wherein the pH of the emulsion is within 1.0 pH units of the dissociation constant (pKa) of the alpha hydroxy acid.

15. The emulsion of claim 14 wherein the pH of the emulsion is within 0.5 pH units of the dissociation constant (pKa) of the alpha hydroxy acid.

16. The emulsion of claim 1 wherein the alpha hydroxy acid is glycolic acid.

17. The emulsion of claim 1 which is free of strontium.

18. A method for treating skin comprising topically applying to the skin of an individual in need thereof an oil-in-water emulsion containing an external aqueous phase and droplets consisting of an oil phase dispersed within the external aqueous phase, which emulsion comprises an alpha-hydroxy acid at a concentration of at least 8.0% w/w, wherein the oil phase of the emulsion comprises a polar emollient and an emulsifier, wherein at least 80% w/w of the constituents of the oil phase of the emulsion, based on the relative amounts of each constituent as used to formulate the emulsion, are polar.

19. The method of claim 18 wherein the emulsifier is cationic, non-ionic, or weakly anionic.

20. The method of claim 18 wherein the emulsion is free of strong anionic emulsifiers.

21. The method of claim 18 wherein at least 85% w/w of the constituents of the oil phase of the emulsion are polar.

22. The method of claim 18 wherein at least 90% w/w of the constituents of the oil phase of the emulsion are polar.

23. The method of claim 18 wherein at least 95% w/w of the constituents of the oil phase of the emulsion are polar.

24. The method of claim 18 wherein the oil phase of the emulsion is free of constituents that are not polar.

25. The method of claim 18 wherein the concentration of the alpha-hydroxy acid in the emulsion is at least 10% w/w.

26. The method of claim 18 wherein the concentration of the alpha-hydroxy acid in the emulsion is at least 12% w/w.

27. The method of claim 18 wherein the emulsion is free of mineral oil, petrolatum, and silicone oil.

28. The method of claim 18 wherein the emulsion is free of non-polar emollients.

29. The method of claim 18 wherein the pH of the emulsion is within 1.0 pH units of the dissociation constant (pKa) of the alpha hydroxy acid.

30. The method of claim 29 wherein the pH of the emulsion is within 0.5 pH units of the dissociation constant (pKa) of the alpha hydroxy acid.

31. The method of claim 18 wherein the alpha hydroxy acid is glycolic acid.

32. The emulsion of claim 1 wherein each of the constituents of the oil phase has a solubility parameter higher than 7.5.

33. The emulsion of claim 32 wherein each of the constituents of the oil phase has a solubility parameter of 8.0 or higher.

34. The emulsion of claim 33 wherein each of the constituents of the oil phase has a solubility parameter of 8.5 or higher.

35. An oil-in-water emulsion containing an external aqueous phase and an internal phase dispersed within the external aqueous phase, wherein the dispersed phase comprises an oil phase and does not comprise a distinct aqueous area within the oil phase, which emulsion comprises an alpha-hydroxy acid at a concentration of at least 8.0% w/w, wherein the oil phase of the emulsion comprises a polar emollient and an emulsifier, wherein at least 80% w/w of the constituents of the oil phase of the emulsion, based on the relative amounts of each constituent as used to formulate the emulsion, are polar.

36. An oil-in-water emulsion containing an aqueous phase and an oil phase wherein the aqueous phase is continuous and the oil phase is dispersed within the continuous aqueous phase and wherein the emulsion does not contain a distinct aqueous phase dispersed within the continuous aqueous phase, which emulsion comprises an alpha-hydroxy acid at a concentration of at least 8.0% w/w, wherein the oil phase of the emulsion comprises a polar emollient and an emulsifier, wherein at least 80% w/w of the constituents of the oil phase of the emulsion, based on the relative amounts of each constituent as used to formulate the emulsion, are polar.

37. An oil-in-water emulsion containing a continuous phase and a dispersed phase within the continuous phase, wherein the continuous phase is an aqueous phase and wherein the dispersed phase consists of an oil phase, which emulsion comprises an alpha-hydroxy acid at a concentration of at least 8.0% w/w, wherein the oil phase of the emulsion comprises a polar emollient and an emulsifier, wherein at least 80% w/w of the constituents of the oil phase of the emulsion, based on the relative amounts of each constituent as used to formulate the emulsion, are polar.

38. An oil-in-water emulsion comprising an external aqueous phase and an internal oil phase dispersed within the external aqueous phase, which emulsion comprises an alpha-hydroxy acid at a concentration of at least 8.0% w/w, wherein the oil phase of the emulsion comprises a polar emollient and an emulsifier, wherein at least 80% w/w of the constituents of the oil phase of the emulsion, based on the relative amounts of each constituent as used to formulate the emulsion, are polar, and wherein the emulsion is not a multivesicular emulsion.

\* \* \* \* \*